United States Patent

Kaufman et al.

[11] Patent Number: 6,043,204
[45] Date of Patent: Mar. 28, 2000

[54] BODY CLEANSING COMPOSITION PROVIDING PROTECTION AGAINST SUNBURN AFTER RINSING

[76] Inventors: Stacy R. Kaufman, 3757 Oak Ridge La., Weston, Fla. 33331; Michael Dulak, 9227 NW. 44 Ct., Coral Springs, Fla. 33065

[21] Appl. No.: 09/187,085

[22] Filed: Nov. 5, 1998

Related U.S. Application Data

[60] Provisional application No. 60/064,766, Nov. 7, 1997, and provisional application No. 60/097,234, Aug. 20, 1998.

[51] Int. Cl.⁷ .............................. A61K 7/50; A61K 7/42; A61K 7/44
[52] U.S. Cl. ................................ 510/130; 424/59; 424/60
[58] Field of Search ............................ 510/130; 424/60, 424/70.1, 59

[56] References Cited

U.S. PATENT DOCUMENTS

| | | |
|---|---|---|
| 4,335,104 | 6/1982 | VanCleave . |
| 4,567,038 | 1/1986 | Ciaudelli et al. . |
| 4,606,913 | 8/1986 | Aronson et al. . |
| 4,701,321 | 10/1987 | Bernstein . |
| 4,933,174 | 6/1990 | Bernstein . |
| 5,041,281 | 8/1991 | Strobridge . |
| 5,186,928 | 2/1993 | Birtwistle . |
| 5,372,804 | 12/1994 | Khoshdel et al. . |
| 5,540,853 | 7/1996 | Trinh et al. ............................ 510/101 |
| 5,607,980 | 3/1997 | McAtee et al. . |
| 5,770,183 | 6/1998 | Linares . |

*Primary Examiner*—Necholus Ogden
*Attorney, Agent, or Firm*—Robert M. Schwartz

[57] ABSTRACT

Disclosed in a body cleansing composition providing upon a single application protection against sunburn measured by Sun Protection Factor (SPF) of at least 15 as applied and SPF of at least 4, and preferably at least 5, after rinsing, consisting essentially of water; at icast onc first sunscreen compound which is a paramethoxycinnamate ester, and at least one second sunscreen compound able to absorb at least 50% of incident radiation at wave lengths from 290 to 320 nanometers; a combination of at least two surface active agents including a first anionic agent which can be an alkyl sulfate salt or an alkoxylated alkyl sulfate salt, and a second agent which can be nonionic, anionic or zwitterionic; at least one hydroxyethylated organic nitrogen compound fixative to enhance retention of SPF on the user's skin selected from the group consisting of N-(2-hydroxyethyl)lactamide and a polymeric quaternary ammonium salt having a plurality of quaternary ammonium groups and at least one 2-hydroxyethyl group; and at least one additive selected firom the group consisting of non-aggressive volatile organic liquids boiling within the range of 15 to 60øC, water-immiscible non-volatile organic carriers, and preservatives able to retard microbial spoilage, whereby protection against sunburn is imparted to a person in need thereof in a single application.

30 Claims, No Drawings

BODY CLEANSING COMPOSITION PROVIDING PROTECTION AGAINST SUNBURN AFTER RINSING

CROSS-REFERENCES TO RELATED APPLICATIONS

This application claims the benefit of U.S. Provisional Application Ser. No. 60/064,766, filed Nov. 7, 1997, and Provisional Application Ser. No. 60/097,234, filed Aug. 20, 1998.

BACKGROUND OF THE INVENTION

1. Field of the Invention

This invention relates to a body cleansing composition containing sunscreen material whose use in bathing or showering imparts protection against sunburn measured by Sun Protection Factor (SPF) as applied at least 15 and after rinsing at least 4, and to a method of imparting protection against sunburn by the application of such composition.

2. Prior Art

It is generally understood that people's ideas about one's ideal appearance change with time. At a time when most heavy work was done outdoors in the sun, as in farming and construction, a sun-bronzed appearance was the mark of the laborer and conversely a light "peaches and cream" complexion was considered emblematic of the leisure class. More recently, as work activities have increasingly moved indoors, the "healthy suntan" look has come to be appreciated as a status symbol, and from seaside resort to suburban backyard to apartment house roof people have deliberately exposed their bodies to the sun, and sometimes to sun-simulating ultraviolet devices, in order to acquire the desired suntan. Unfortunately, many light skinned people have experienced uncomfortable and even dangerous sunburns instead of the desired tan. This has given rise to a demand for products to apply to a person's skin in order to provide protection against sunburn while interfering as little as possible with the acquisition of a tan. One such product has long been promoted with the slogan "Tan, don't burn, with _____".

Such products typically contain a selective ultraviolet absorber or sunscreen, that is a compound with the ability to absorb a large fraction of the sunshine radiation of those wave-lengths believed to be responsible for burning of the skin, namely 290–320 nanometers, while allowing the passage of most of the longer wave length radiation believed to be beneficial for tanning. These sunscreens are typically formulated in products suitable for application to human skin and desirably able to provide protection for as long as needed. A substantial body of art has accumulated as formulators have endeavored to provide safe, effective, long lasting and cosmetically elegant products.

Van Cleave U.S. Pat. No. 4,335,104 discloses a multi-purpose anhydrous cosmetic composition comprising a major portion of a water insoluble non-ionic surfactant with HLB of 12 or less, in combination with a small but effective amount of an active ingredient soluble in the surfactant. For use as a suntan lotion, the composition includes a sunscreen as the active ingredient, along with a diluent such as propylene glycol, an emollient such as isopropyl myristate and a preservative. The disclosed anhydrous product is stated to have numerous advantages compared to products containing water.

Ciaudelli et al U.S. Pat. No. 4,567,038 discloses a sunscreen mousse product which, when applied to a person's hair, blocks or reduces the amount of radiation reaching the hair and thereby inhibits bleaching of the hair. The mousse base comprises a cationic surfactant substantive to the hair by electrostatic attraction and a nonionic resin film-former to coat and thereby provide holding effect to the hair in alcohol and water. The sunscreen agents in the composition must be at least water miscible and preferably water soluble for compatibility with the mousse. Disclosed presentation of the composition is in cans pressurized with propellents using conventional techniques.

Aronson et al U.S. Pat. No. 4,606,913 discloses electrolyte stabilized high internal phase emulsions (HIPE) which can contain sunscreen agents. HIPE are defined as oil-in-water emulsions containing at least 75% of internal oil phase and water-in-oil emulsions containing at least 75% of internal aqueous phase. Thus a sunscreen cream is stated to contain an internal phase of water, an external phase of mineral oil, and uv screening agent, and a "waterproof suntan cream" is formulated with an internal phase of water, an external phase of mineral oil/silicone oil, sunscreen agent and perfume. Aronson's emulsifiers are non-ionic materials with HLB of 1 to 7, preferably 2 to 6.

Bernstein U.S. Pat. Nos. 4,701,321 and 4,933,174 discloses incorporation of sunscreen into nonionic and amphoteric liquid detergents so that repeated washing and bathing with such detergents leaves a long-lasting substantive and effective amount of the incorporated sunscreen in the stratum corneum of the skin. Previous attempts to incorporate sunscreen into soap are said to have failed because ionic soaps would rapidly degrade the incorporated sunscreen. Effectiveness is shown of compositions applied to the skin of human subjects repeatedly, such as 12 times during a six hour period, twice daily for ten days, or once daily for four weeks, before being subjected to solar or artificial ultraviolet exposure.

Strobridge U.S. Pat. No. 5,041,281 discloses an oil-in-water emulsion sunscreen composition including between about 0.5 and about 20 weight per cent of a copolymer of ethylene and vinyl acetate, and a second film forming polymer which increases the substantivity of the composition and is present at between about 0.5 and about 10 percent. The composition is stated to have improved substantivity in water.

Birtwhistle U.S. Pat. No. 5,186,928 discloses a hair shampoo comprising water, an anionic surfactant, a water-insoluble sunscreen, a cationic derivative of a polygalactomannan gum and, when the sunscreen is in the form of a solid at 20øC, an non-volatile solvent for the solid sunscreen. The composition is stated to enable enhanced levels of sunscreen to be deposited on hair surfaces.

Khoshdel et al U.S. Pat. No. 5,372,804 discloses a cosmetic composition comprising at least one cosmetic agent for deposition onto hair or skin, and as a carrier for the agent, latex particles of a polymer material having a particle size of less than about 1 micron. The cosmetic agent can be a sunscreen present in the compositions, for example, in an amount of from about 0.1 to 5% by weight. Additional components normally found in cosmetic compositions for the hair or the skin can be present, including one or more surfactants, preferably selected from anionic, nonionic, amphoteric and zwitterionic surfactants, present in the compositions in an amount of from 1 to 70% by weight, preferably from 2 to 40%.

McAtee et al U.S. Pat. No. 5,607,980 discloses compositions for topical application to human skin for improved skin feel, in the form of leave-on products or products that are rinsed or wiped off after use. The compositions comprise from 0.1% to about 20% of an amphoteric surfactant defined by the structural formula

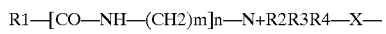

in which R1 is unsubstituted, saturated or unsaturated, straight or branched chain alkyl having from about 9 to about 22 carbon atoms; m is an integer from 1 to about 3, n is 0 or 1; R2 and R3 are independently selected from alkyl having from 1 to about 3 carbon atoms and monohydroxyalkyl having from about 1 to about 3 carbon atoms; R4 is selected from saturated or unsaturated alkyl having from 1 to about 5 carbon atoms and saturated or unsaturated monohydroxyalkyl having from 1 to about 5 carbon atoms; X is selected from the group consisting of CO3, SO3, and SO4 and pharmaceutically acceptable salts of the foregoing compounds; from about 0.1% to about 20% by weight of an anionic surfactant, from about 0.1% to about 15% by weight of a cationic surfactant, and from about 45% to about 99.7% by weight of water. The composition can comprise a wide range of additional components spanning the alphabet from abrasives to viscosity increasing agents and including mention of sunscreen agents and ultraviolet light absorbers.

Linares U.S. Pat. No. 5,770,183 discloses a waterproof water-in-oil emulsion sunblock composition wherein the aqueous phase consists predominantly of deionized water and the oil phase includes sunscreen active ingredients, silicone emulsifiers, oil soluble solubilizers and skin conditioning agents. The emulsion provides sun protection higher than SPF 30 and is characterized by a mean particle size of the oil phase ingredients of 2 microns.

Gers-Barlag et al German published specification 19,548,016 dated Jun. 26, 1997 discloses sunscreen oil-in-water and water-in-oil emulsions with lipophilicity which depends on pH and temperature such that lipophilicity increases with increasing temperature.

Absent from all the above disclosures is any suggestion of a composition applied to the body in bathing or showering and able to impart in a single application thereof adequate protection from sunburn upon exposure to natural or artificial sources of ultraviolet radiation.

SUMMARY OF THE INVENTION

In accordance with this invention, a body cleansing composition providing upon a single application protection against sunburn measured by Sun Protection Factor (SPF) of at least 15 as applied and SPF of at least 4, and preferably at least 5, after rinsing consists essentially of water; at least one first sunscreen compound which is a paramethoxycinnamate ester, and at least one second sunscreen compound able to absorb at least 50% of incident radiation at wave lengths from 290 to 320 nanometers; a combination of at least two surface active agents including a first anionic agent which can be an alkyl sulfate salt or an alkoxylated alkyl sulfate salt, and a second agent which can be nonioinic, anionic or zwitterionic; at least one hydroxyethylated organic nitrogen compound fixative to enhance retention of SPF on the user's skin selected from the group consisting of N-(2-hydroxyethyl)lactamide and a polymeric quaternary ammonium salt having a plurality of quaternary ammonium groups and at least one 2-hydroxyethyl group; and at least one additive selected from the group consisting of non-aggressive volatile organic liquids boiling within the range of 15 to 60øC, water-immiscible non-volatile organic carriers, and preservatives able to retard microbial spoilage, whereby protection against sunburn is imparted to a person in need thereof in a single application.

The term "consisting essentially of" is used in its art-recognized meaning to indicate that the composition is open to the inclusion of only such additional ingredients as do not adversely affect the advantageous properties of the composition. The term "non-aggressive" is used to indicate that strongly irritating, odorous, toxic or chemically reactive volatile organic liquids boiling within the stated range are excluded. Among such excluded volatile organic liquids are acetyl chloride, ethyl methyl sulfide, hydrogen cyanide, and isoprene.

When the composition of the invention contains a volatile liquid additive boiling in the range from 15 to 60øC, the composition is quiescent in its shipping and storage container whether open or closed, and begins to froth when poured out if its container on the user's body or other air exposed surface and thereby affords a refreshing sensation, and also imparts in a single use as in bathing or showering sufficient sunscreen to leave a person well protected even after normal rinsing and drying. With or without such volatile liquid additive the composition is well suited to presentation in simple non-pressurized containers but can also be presented as pressurized aerosol with addition of a suitable propellant.

DESCRIPTION OF PREFERRED EMBODIMENTS

SPF values for compositions such as those of this invention, as well as control compositions without sunscreen and compositions containing known standards, can be measured according to a procedure recommended by the US Food and Drug Administration and published in the Federal Register, vol. 43, pages 38264–38267, 1978.

The light source employed is a 150 watt Xenon Arc Solar Simulator (Solar Light Co, Philadelphia Pa.) having a continuous emission spectrum in the UV-B range from 290 to 320 nanometers.

According to the above mentioned procedure, there is first determined a Minimal Erythema Dose (MED) for each subject by exposing the subject's unprotected back to a series of timed incremental UV exposures at 25% intervals. The subject's MED is the shortest time of exposure that produces minimally perceptible crythema at 20 to 24 hours post irradiation. A homosalate standard or any test material whose SPF is to be determined is delivered to a defined area test site by syringe and the protected MED determined. To determine the water resistance of a test material, a rinse can be included after application of the material. The SPF is calculated according to the equation $$SPF = \frac{MED \text{ Protected Skin}}{MED \text{ Unprotected Skin}}$$

A sunscreen compound is defined as a compound that absorbs at least 85% of incident radiation at wave lengths of 290 to 320 nanometers and may or may not absorb radiation at wave lengths greater than 320 nanometers.

Preferred p-methoxycinnamic acid ester first sunscreen compounds include amyl p-methoxycinnamate, 2-ethylhexyl p-methoxycinnamate, 2-ethoxyethyl p-methoxycinnamate, diethanolamine p-methoxycinnamate, n-octyl p-methoxycinnamate and propyl p-methoxycinnamate.

Second sunscreen compounds recognized as safe and effective by the US Food and Drug Administration include p-aminobenzoic acid, Cinoxate, Avobenzone, digalloyl trioleate, dioxybenzone, ethyl 4- [bis(hydroxypropyl)] aminobenzoate, glyceryl aminobenzoate, homosalate, lawsone with dihydroxyacetone, menthyl anthranilate, octocrylene ethyl 2-cyano-3,3-diphenyl acrylate, octyl salicylate, oxybenzone, Padimate O, phenylbenzimidazole sulfonic acid, red petrolatum, sulisobenzone, titanium dioxide, zinc oxide, including regular grades and grades of such fine particle size as enable the composition to be translucent or transparent, and triethanolamine salicylate. Additional sunscreen compounds recognized by European authorities include N,N,N-trimethyl-4-(2-oxoborn-3-ylidene methyl) anilinium methyl sulfate, 3-imidazol-4-ylacrylic acid and its ethyl ester, 2-phenylbenzimidazole-5-sulfonic acid and its salts, ethoxylated 4-aminobenzoic acid, amyl 4-dimethylaminobenzoate, 3,3,5-trimethylcyclohexyl-2-acetamidobenzoate, potassium cinnamate, 4-methoxycinnamic acid salts, propyl 4-methoxycinnamate, salicylic acid salts, amyl 4-methoxycinnamate, mexenone, sulisobenzone, 2-ethylhexyl 2-(4-phenylbenzoyl)-benzoate, 5-methyl-2-phenylbenzoxazole, sodium 3,4-dimethoxyphenylglyoxylate, 1,3-bis(4-methoxyphenyl) propane-1,3-dione, 5-(3,3-dimethyl-2-norbornylidene)-3-penten-2-one, alpha-(2-oxoborn-3-ylidene)-p-xylene-2-sulfonic acid, alpha-(2-oxoborn-3-ylidene)toluene-4-sulfonic acid and its salts, 3-(4-methylbenzylidene)bornan-2-one, 3-benzylidenebornan-2-one, alpha-cyano-4-methoxycinnamic acid and its hexyl ester, 1-p-cumenyl-3-phenylpropane-1,-3-dione, 4-isopropylbenzyl salicylate, cyclohexyl 4-methoxycinnamate, and 1-(4-t-butylphenyl)-3-(4-methoxyphenyl)propane-1,3-dione.

Preferred para-methoxycinnamate ester first sunscreen compounds include the the methyl, ethyl, 2-ethylhexyl, heptyl, n-octyl, isooctyl, isodecyl and lauryl esters of p-methoxycinnamic acid and mixtures thereof.

Preferred second sunscreen compounds include sunscreen compounds selected from the group consisting of a 2-hydroxy-4-alkoxybenzophenone, a dibenzoylmethane compound, a salicylic acid ester, zinc oxide and mixtures thereof.

Particularly preferred salicylate ester sunscreen compounds include 2-ethylhexyl salicylate, lauryl salicylate, n-octyl salicylate, and p-octylphenyl salicylate and mixtures thereof.

Particularly preferred 2-hydroxy-4-alkoxybenzophenone sunscreen compounds include 2-hydroxy-4-methoxybenzophenone, 2-hydroxy-n-octoxybenzophenone, 2-hydroxy-4-dodecyloxybenzophenone and mixtures thereof.

Particularly preferred 1,3-diphenylpropane-1,3-dione (also known as dibenzoylmethane) sunscreen compounds include 1,3-bis(4-methoxyphenyl)propane-1,3-dione, 1-(4-t-butylphenyl)-3-(4methoxyphenyl)propane-1,3-dione, 1-p-cumenyl-3-phenylpropane-1,-3-dione and mixtures thereof.

Zinc oxide when present is preferably of a fine particle size in the range from 2 to 50 microns and can be surface coated to facilitate dispersion.

The quantity of water in the composition is in the range from 30 to 90 parts by weight.

The total level of first and second sunscreen agents in the composition can be in the range of 3 to 40 parts by weight, preferably 6 to 19 parts by weight, and the proportions of first and second sunscreen agents are preferably in the range from 3:1 to 1:3. The test method described herein provides means for establishing the use level required for the desired effect and avoiding wasteful and unnecessary overuse of this ingredient.

First anionic cleansing agents according to this invention include alkyl sulfate salts, alkyl ethoxylate sulfate salts, alkylphenyl ethoxylate sulfate salts and mixtures thereof. Preferred salts include potassium, sodium, ammonium, and triethanolamine salts. Particularly preferred first anionic cleansing agents include alkali metal and ammonium lauryl sulfates, sodium lauryl ether (2EO) sulfate, sodium lauryl ether (3EO) sulfate, sodium C10–C16 alkyl ether sulfate, sodium laureth sulfate, among which sodium alkyl ether sulfates are most preferred.

Second cleansing agents according to this invention when anionic include alpha olefin sulfonate salts, alkylbenzenesulfonate salts, alkali metal fatty acylisethionates having 8 to 18 carbon atoms in the fatty acyl group, and mixtures thereof in addition to the above.

The level of anionic cleansing agent in the composition can be in the range of 3 to 15 parts by weight, preferably 4 to 13 parts by weight when a plurality of anionic cleansing agents is used and 3 to 6 parts by weight when a single anionic cleansing agent is used together with a nonionic or zwitterionic cleansing agent. The test method described herein provides means for establishing the use level required for the desired effect and avoiding wasteful and unnecessary overuse of this ingredient.

Preferred second cleansing agents when nonionic include 8 to 18 carbon atom fatty acid monoglycerides and diglycerides, sorbitan esters of 8 to 18 carbon atom fatty acids and ethoxylated derivatives thereof ethoxylated alcohols having 9 to 16 carbon atoms in the alkyl group and 4 to 14 or 20 to 30 units of ethylene oxide, and polyoxypropylenepolyoxyethylene copolymers (CTFA namne Poloxamer).

Preferred second cleansing agents when zwitterionic include fatty acylamidopropyl betaine and fatty acylamidopropyl hydroxysultaine having 1 to 18 carbon atoms in the fatty acyl group and mixtures thereof. The level of zwittenionic cleansing agent in the composition can be in the range of 1 to 10% by weight, preferably 2 to 6% by weight. The test method described herein provides means for establishing the use level required for the desired effect and avoiding wasteful and unnecessary overuse of this ingredient.

The fixatives that enhance SPF and the retention of SPF according to this invention are characterized by at least one amine or amide nitrogen, which can be substituted or quatenized, a plurality of quaternary ammonium nitrogen atoms and a tenninal hydroxyethyl group. Preferred fixatives that fit this description include N-2-hydroxyethyllactamide, water soluble quaternary ammonium compounds having a plurality of quaternary ammonium groups and at least one 2-hydroxyethyl group, and polymeric quaternary ammonium derivative of hydroxyethyl cellulose. Particularly preferred are certain members of a class of multi-functional quaternary ammonium compounds to which the CTFA designated name POLYQUATERNIUM (followed by a number) has been applied, as shown in Table 1, among which POLYQUATERNIUM 10 is most especially preferred.

TABLE 1

| | |
|---|---|
| POLYQUATERNIUM 1 | POLYMERIC 2-BUTEN-1,4-DIYL DIMETHYLAMMONIUM CHLORIDE TERMINATED WITH TRIETHANOLAMMONIUM QUATERNARY GROUPS |
| POLYQUATERNIUM 4 | COPOLYMER OF HYDROXYETHYLCELLULOSE AND DIALLYLDIMETHYLAMMONIUM CHLORIDE |
| POLYQUATERNIUM 10 | POLYMERIC QUATERNARY AMMONIUM SALT OF HYDROXYETHYL CELLULOSE REACTED WITH TRIMETHYLAMMONIUM SUBSTITUTED EPOXIDE |
| POLYQUATERNIUM 24 | POLYMERIC QUATERNARY AMMONIUM SALT OF HYDROXYETHYL CELLULOSE REACTED WITH LAURYLDIMETHYLAMMONIUM SUBSTITUTED EPOXIDE |

The level of such fixative in the composition can be in the range of 0.1 parts to 12 parts by weight, preferably 0.1 to 1 parts by weight of a multifunctional 2-hydroxyethyl quaternary ammonium compound and 0.1 to 12 parts by weight of N-(2-hydroxyethyl)lactamide. Excessive amounts of multifuctional 2-hydroxyethyl quaternary ammonium compound are undesirable and wasteful, and can contribute to excessively viscous solutions and products that feel tacky.

Non-aggressive volatile organic compounds used as additives according to this invention can be water soluble or water insoluble and include aliphatic and cycloaliphatic hydrocarbons such as 2-methylbutane, n-pentane, 2,2-dimethylpropane, 1,1-dimethylcyclopropane and 2,2-dimethylbutane; open chain and cyclic oxygenated organic compounds such as dimethoxymethane, methyl formate, ethyl formate, furan, methyl t-butyl ether, propylene oxide and diethyl ether; and polyhalogenated organic compounds in which at least one halogen is fluorine such as 2-chloro-1,1-difluoroethane, 1,3-dichloro-1,1,2,2,3-pentafluoropropane, 1,1-dichloro-2,2,2-trifluoroethane, 1,2-dichloro-1,1,2-trifluoroethane, 1,2-dichloro-1,2-difluoroethane, 1,1-dichloro-2-2-difluoroethane, 1,2-dichloro-1,1-difluoroethane, 1,2-difluoroethane, 1,1,2-trichloro-1,2,2-trifluoroethane, 1-fluoro-1,1-dichloroethane and mixtures thereof. The quantity of volatile organic compound is in the range from 0 to 12 parts by weight, preferably from 3 to 10 parts by weight.

Water-immiscible non-volatile organic carriers used as additives according to this invention can be liquid or solid emulsifiable materials and include fatty glycerides such as lard oil, olive oil, canola oil, soybean oil, medium chain triglyceride, acetylated mono-and diglyccride and glycerol monooleate; high molecular weight hydrocarbons with at least 30 carbon atoms such as paraffin wax, microcrystalline wax, mineral oil, gelled mineral oil, petrolatum, and hydrogenated oligomers of 1-decene; silicone oils and modified silicones such as dimethicone, cyclomethicone, alkoxylated hydroxypropyl(polydimethylsiloxanes) and cyclomethicone and dimethicone copolyol (CTFA) products; phospholipids such as lecithin, phosphatidylcholine and phosphatidylserine; emulsifiable oxidized waxes and oxidized polyethylenes; copolymers of 1-olefins with unsaturated carboxylate esters, dicarboxylic acids and their anhydrides, and unsaturated lactams, such as 1-octadecene—maleic anhydride and 1-eicosene—vinylpyrrolidone copolymers; and open chain or cyclic high molecular weight esters having 16 to 60 carbon atoms such as cetyl palmitate, dibutyl sebacate, di-isononyl adipate, dihexyl phthalate, isopropyl myristate, isopropyl palmitate, methyl stearate, mixed long chain alkyl benzoates, butyl epoxystearate and epoxidized soybean oil and mixtures thereof. When present, the quantity of water insoluble non-volatile carrier is in the range from 0 to 25 parts by weight, when present preferably from 3 to 19%.

Preservatives used as additives according to this invention are preferably free of heavy metals and can be polyfunctional acids and their alkali metal and ammonium salts such as citric acid, tartaric acid, phosphoric acid, iminodiacetic acid, nitrilotriacetic acid, hydroxyethyleneaminodiacetic acid and ethylenediaminetetraacetic acid and salts thereof; para-hydroxybenzoates such as butyl paraben, methyl paraben and propyl paraben; imidiazolinylurea, triclosan, dimethyloldimethylhydantoin, isothiazolidinone compounds and mixtures thereof. When present, the quantity of preservative in the range from 0.001 to 2 parts by weight, preferably from 0.01 to 0.2 parts by weight.

Among additional ingredients that can be included in the composition of this invention as needed there can be included fragrances; foam boosters such as lauryldimethylamine oxide and fatty alkanolamides; clarifyiers, gelling agents, moisturizers such as glycerin, propylene glycol and butylene glycol; thickeners such as polyethylene glycol 6000 distearate; emollients such as silicone and aloe vera, vitamins such as Vitamin A, Vitamin C and Vitamin E, alpha-hydroxy acids such as glycolic acid and lactic acid, and pigments and colors for pearlescent, metallic, gold and other esthetic effects. Ingredients of satisfactory quality for the preparation of compositions according to the invention are commercially available and can be compounded by conventional procedures including emulsification as required at any convenient temperature at which water is liquid.

It is a feature of this invention that the composition can be formulated at a pH that allows the composition to be mild to the skin, suitably within the range of 3.0 to 7.5.

As formulated for use, the quantity of composition used in a single application preferably ranges from 5 to 100 grams. Typically, the user applies the desired quantity to the dry or wet skin in the course of bathing or showering, allows it to remain on the skin for a dwell period of 15 seconds to about 5 minutes, lathers and massages, and rinses off.

Packaging and presentation can take a variety of forms including simple glass and plastic bottles, decorative cream jars, squeeze tubes, and foil pouches holding a single use quantity. The composition of the invention can also be presented as an aerosol in conventional aluminum or steel aerosol containers with the addition of a suitable propellant. Fluorotrichloromethane propellant can be used where regulations permit; elsewhere, isobutane, dimethyl ether, 1,1-difluoro-1-chloroethane and other ecologically acceptable replacement candidates are suitable.

EXAMPLES 1–5

Body cleanser preparations were formulated as shown in TABLE 2 below and tested by the method described below combining the measurement of static SPF and retention of SPF after a specified rinse test.

The light source employed was a 150 watt Xenon Arc Solar Simulator (Solar Light Co, Philadelphia Pa.) having a continuous emission spectrum in the UV-B range from 290 to 320 nm. The device is equipped with a dichroic mirror which reflects all radiation below 400 nm and works in conjunction with a 1 mm thick Schott WG-320 filter absorbing all radiation below 290 nm to produce simulation of the solar UVA-UVB spectrum. A 1 mm thick UG 5 or UG 11 filter (black lens) was added to remove reflected (infra-red, >700 nm) heat and remaining visible radiation. UV exposure was monitored continuously during exposure using a Model DCS-1 Sunburn UV Meter/Dose Controller System. Measurements were taken at a position within 8 mm from the surface of the skin. The field of irradiation was 1 cm in diameter.

The procedure for the measurement of SPF was that outlined in Federal Register vol. 43, pages 38264–267 (1978) with the modification shown below One test area served to determine each subject's Minimal Erythema Dose (MED). This was executed by exposing the back to a series of timed incremental UV exposures at 25% intervals. The individual subject's MED is the shortest time of exposure that produces minimally perceptible erythema at 20 to 24 hours post irradiation. The test area is described as the infrascapular area of the back to the right and left of the midline.

An 8% homosalate standard was delivered to the defined area test site through volumetric plastic syringes. The material was then evenly applied to a rectangular area measuring 5 cm by 10 cm for 50 square centimeter area for a final concentration of 2 milligram per square centimeter.

Fifteen minutes after application, a series of UV light exposures in 25% increments calculated from previously determined MED's bracketing the intended SPF were administered from the solar simulator to subsites within the treated area. On the actual day of testing another series of exposures similar to the one given on the previous day was administered to an adjacent untreated site of unprotected skin to redetermine the MED. An adjacent test site was then selected to perform a static determination on the test substance. In order to test for retention of SPF at the same time, the protocol was modified to select an additional test site for each test material, wherein test materials were applied to moistened back using 0.05 ml of water and rubbed into a lather. Test sites were then rinsed with approximately 3.0 ml of water until removal of lather (approximately 1 minute). UV exposures were begun immediately following this procedure.

Twenty to twenty four hours post exposure, the subjects were instructed to return to the testing facility for evaluation of delayed erythemic response. The smallest exposure or the least amount of energy required to produce erythema (MED) in the treated site was recorded. The SPF was then calculated according to the equation $$SPF = \frac{MED \text{ Protected Skin}}{MED \text{ Unprotected Skin}}$$

In the following TABLE 2 of formulation ingredients for each example and SPF results obtained, all parts are by weight of active ingredient.

TABLE 2

| Ingredient | CONTROL A | 1 | 2 | 3 | 4 | 5 |
|---|---|---|---|---|---|---|
| Sunscreens: | | | | | | |
| 2-ethylhexyl p-methoxy-cinnamate | 7.5 | 4.75 | 7.5 | 7.5 | 4.75 | 7.5 |
| octyl salicylate | none | none | 5 | 5 | none | 5 |
| 2-hydroxy-4-methoxy-benzophenone | 6 | 4 | 6 | 6 | 4 | 6 |
| Anionic cleansing agents: | | | | | | |
| Ammonium lauryl sulfate | 6 | 6.0 | 8.3 | 8.3 | 6 | 8.3 |
| Sodium cocoyl isethionate | 1.67 | 1.67 | 1.8 | 1.8 | 1.67 | 1.8 |
| Zwitterionic cleansing agents: | | | | | | |
| Cocoylamido-propylhydroxy-sultaine | 2.5 | 2.5 | 2.5 | 2.5 | 2.5 | 2.5 |
| Fixatives: | | | | | | |
| N-(2-hydroxy-ethyl)lactamide | none | none | 5 | none | none | 5 |
| Polyquaternium 10 | none | 0.3 | 0.5 | 0.5 | 0.6 | 0.5 |
| Preservatives: | | | | | | |
| Tetrasodium EDTA | 0.2 | 0.2 | 0.2 | 0.2 | 0.2 | 0.2 |
| Methyl paraben | 0.2 | 0.2 | 0.2 | 0.2 | 0.2 | 0.2 |
| Imidazo-lidinylurea | 0.2 | 0.2 | 0.2 | 0.2 | 0.2 | 0.2 |
| Dimethyloldi-methyl-hydantoin | 0.1 | 0.1 | 0.1 | 0.1 | 0.1 | 0.1 |
| Other ingredients: | | | | | | |
| Soy fatty acyldiethan-olamide | 0.8 | 0.8 | none | none | 0.8 | none |
| Propylene glycol | 0.2 | 0.2 | 0.2 | 0.2 | 0.2 | 0.2 |
| N-vinylpyrroli-done/1-eicosene copolymer | none | none | none | 3 | none | 1.5 |
| fragrance | 0.6 | 0.6 | none | none | none | none |
| Dimethicone 344FL | none | none | none | none | none | none |
| titanium dioxide | none | none | none | none | none | none |
| water | to 100 | to 100 | to 100 | to 100 | to 100 | to 100 |
| pH | 6.0 | 6.0 | 6.0 | 6.0 | 6.0 | 6.00 |
| Static SPF | 20.6 | 16.5 | 28.7 | 32.1 | 25.7 | 21.5 |
| SPF after rinse | 3.5 | 8.5 | 8.4 | 9.5 | 9.4 | 11.0 |

The homosalate standard tested in the same way had static SPF 4.67 without rinse and was not tested with rinse.

As shown by these results, the compositions of the invention achieve the objective of imparting in a single application sufficient sunscreen to leave a person well protected even after a rinse test simulating real life conditions of bathing, showering, and rinsing in removing sunscreen from the skin. Accordingly, finding after such exposure a level of protection far greater than that of a standard without any rinse or a control composition lacking fixative and otherwise comparable is dramatic and unexpected.

EXAMPLES 6–9

Body cleanser preparations were formulated as shown in TABLE 3 below and tested by the procedure described above.

TABLE 3

| Ingredient | EXAMPLE | | | |
|---|---|---|---|---|
| | 6 | 7 | 8 | 9 |
| Sunscreens: | | | | |
| 2-ethylhexyl p-methoxy-cinnamate | 7.5 | 7.5 | 7.5 | 7.5 |
| octyl salicylate | 5 | 5 | 5 | 5 |
| 2-hydroxy-4-methoxy-benzophenone | none | none | 6 | 6 |
| Anionic cleansing agents: | | | | |
| Sodium Lauryl sulfate | 3.85 | 3.85 | 3.85 | 3.85 |
| Zwitterionic cleansing agent: | | | | |
| Cocoyl-amidopropl-betaine | 3.33 | 3.33 | 3.33 | 3.33 |
| Fixative: | | | | |
| N-(2-hydroxyethyl)lactamide | 5 | 10 | none | 2.5 |
| Polyquaternium 10 | none | none | 0.5 | none |
| Preservative: KATHON CG isothiazolidinone compound | 0.04 | 0.04 | 0.04 | 0.04 |
| Other ingredients: | | | | |
| Cocoyldi-ethanolamide | 3.33 | 3.33 | 3.33 | 3.33 |
| Sodium chloride | none | 0.4 | none | none |
| water | to 100 | to 100 | to 100 | to 100 |
| pH | 6.0 | 6.0 | 6.0 | 6.0 |
| Static SPF | 32.5 | 28.7 | 32.1 | 32.1 |
| SPF after rinse | 9.5 | 8.7 | 13.6 | 10.5 |

The homosalate standard tested in the same way had static SPF 4.67 without rinse and was not tested with rinse.

As shown by these results, the compositions of the invention achieve the objective of imparting in a single application sufficient sunscreen to leave a person well protected even after a rinse test simulating real life conditions of bathing, showering, and rinsing in removing sunscreen from the skin.

EXAMPLE 10

A sunscreen containing body cleanser preparation that frothed upon placing upon the skin was formulated as shown below and tested by the method described above combining the measurement of static SPF and retention of SPF after the specified rinse test. All ingredients are shown in parts by weight.

| Ingredient | |
|---|---|
| Sunscreens: | |
| 2-ethylhexyl p-methoxycinnamate | 5.63 |
| octyl salicylate | 3.75 |
| 2-hydroxy-4-methoxy-benzophenone | 4.5 |
| Anionic cleansing agent: | |
| Sodium Laureth sulfate | 3.85 |
| Sodium lauryl ether sulfate | 1.05 |
| Zwitterionic cleansing agent: | |
| Cocoylamidopropylbetaine | 3.33 |
| Volatile organic liquid: | |
| n-Pentane | 5.0 |
| Non-volatile organic liquid carrier: | |
| Water soluble petrolatum | 4.63 |
| Fixative: | |
| Polyquaternium 10 | 0.5 |
| Preservative: | |
| KATHON CG isothiazolidinone compound | 0.04 |
| Other ingredients: | |
| Cocoyldiethanolamide | 3.33 |
| Lauryl amine oxide | 0.75 |
| Fragrance | 1.0 |
| water | to 100 |
| pH | 6.5 to 7.5 |
| Static SPF | 23.0 |
| SPF after rinse | 7.2 |

The composition was prepared by first combining the sunscreens and petrolatum with gentle warming as needed to dissolve and then adding this blend to a separately prepared blend of the surfactants, homogenizing to a cream, and combining with a solution of water, organic nitrogen compound fixative, preservative, fragrance and other water soluble ingredients and then with the volatile liquid, and packaged in screw cap bottles.

The results show that the composition of the invention achieved the objective of imparting in a single application sufficient sunscreen to leave a person well protected even after a rinse test simulating real life conditions of bathing, showering, and rinsing.

EXAMPLE 11

A sunscreen containing body cleanser preparation that frothed upon placing upon the skin was formulated as shown above and tested by the method described below combining the measurement of static SPF and retention of SPF after the rinse test. All ingredients are shown in parts by weight.

| Ingredient | |
|---|---|
| Sunscreens: | |
| 2-ethylhexyl p-methoxycinnamate | 7.5 |
| 2-hydroxy-4-methoxy-benzophenone | 6.0 |
| Anionic cleansing agent: | |
| Sodium Laureth sulfate | 3.85 |
| Sodium lauryl ether sulfate | 1.05 |
| Zwitterionic cleansing agent: | 3.33 |

-continued

| Ingredient | |
|---|---|
| Cocoylamidopropylbetaine | |
| Volatile organic | 5.0 |
| liquid: n-Pentane | |
| Non-volatile | 5.0 |
| organic liquid carrier: | |
| General Electric SF1528 | |
| Cyclomethicone Dimethicone Copolyol | |
| Fixative: | |
| Polyquaternium 10 | 0.5 |
| Preservative: | 0.04 |
| KATHON CG | |
| isothiazolidinone compound | |
| Other ingredients: | |
| Cocoyldiethanolamide | 3.33 |
| Lauryl amine oxide | 0.75 |
| Fragrance | 1.0 |
| water | to 100 |
| pH | 6.5–7.5 |
| Static SPF | 24.5 |
| SPF after rinse | 8.0 |

The composition was prepared by first combining the sunscreens and SF1528 with gentle warming as needed to dissolve and then adding this blend to a separately prepared blend of the surfactants, homogenizing to a cream, and combining with a solution of water, organic nitrogen compound fixative, preservative, fragrance and other water soluble ingredients and then with the volatile liquid, and packaged in screw cap bottles.

The results show that the composition of the invention achieved the objective of imparting in a single application sufficient sunscreen to leave a person well protected even after a rinse test simulating real life conditions of bathing, showering, and rinsing.

EXAMPLE 12

A sunscreen containing body cleanser preparation that frothed upon placing upon the skin was formulated as shown below and tested by the method described above combining the measurement of static SPF and retention of SPF after a specified rinse test. All ingredients are shown in parts by weight.

| Ingredient | |
|---|---|
| Sunscreens: | |
| 2-ethylhexyl | 5.63 |
| p-methoxycinnamate | |
| octyl salicylate | 3.75 |
| 2-hydroxy-4-methoxy- | 4.5 |
| benzophenone | |
| Anionic cleansing agent: | |
| Sodium Laureth sulfate | 3.85 |
| Sodium lauryl ether sulfate | 1.05 |
| Zwitterionic cleansing agent: | 3.33 |
| Cocoylamidopropylbetaine | |
| Volatile organic | 5.0 |
| liquid: n-Pentane | |
| Non-volatile | 4.63 |
| organic liquid carrier: | |
| Mineral Oil Gel | |
| Fixative: | 0.5 |
| Polyquaternium 10 | |
| Preservative: | 0.04 |

-continued

| Ingredient | |
|---|---|
| KATHON CG | |
| isothiazolidinone compound | |
| Other ingredients: | |
| Cocoyldiethanolamide | 3.33 |
| Lauryl amine oxide | 0.75 |
| Fragrance | 1.0 |
| water | to 100 |
| pH | 6.5–7.5 |

The composition was prepared by first combining the sunscreens and mineral oil gel with gentle warming as needed to dissolve and then adding this blend to a separately prepared blend of the surfactants, homogenizing to a cream, and combining with a solution of water, organic nitrogen compound fixative, preservative, fragrance and other water soluble ingredients and then with the volatile liquid, and packaged in screw cap bottles.

The results show that the composition of the invention achieved the objective of imparting in a single application sufficient sunscreen to leave a person well protected even after a rinse test simulating real life conditions of bathing, showering, and rinsing.

EXAMPLE 13

A sunscreen containing body cleanser preparation that frothed upon placing upon the skin was formulated as shown above and tested by the method described below combining the measurement of static SPF and retention of SPF after the rinse test. All ingredients are shown in parts by weight.

| Ingredient | |
|---|---|
| Sunscreens: | |
| 2-ethylhexyl | 5.63 |
| p-methoxycinnamate | |
| Octyl salicylate | 3.75 |
| 2-hydroxy-4-methoxy- | 4.5 |
| benzophenone | |
| Anionic cleansing agent: | |
| Sodium Laureth sulfate | 3.85 |
| Sodium lauryl ether sulfate | 1.05 |
| Zwitterionic cleansing agent: | 3.33 |
| Cocoylamidopropylbetaine | |
| Volatile organic liquid: | 5.0 |
| n-Pentane | |
| Non-volatile | 4.63 |
| organic liquid carrier: | |
| General Electric SF1528 | |
| Cyclomethicone Dimethicone Copolyol | |
| Fixative: | 0.5 |
| Polyquaternium 10 | |
| Preservative: | 0.04 |
| KATHON CG | |
| isothiazolidinone compound | |
| Other ingredients: | |
| Cocoyldiethanolamide | 3.33 |
| Lauryl amine oxide | 0.75 |
| Fragrance | 1.0 |
| water | to 100 |
| pH | 6.5–7.5 |
| Static SPF | 23.2 |
| SPF after rinse | 6.4 |

The composition was prepared by first combining the sunscreens and SF1528 with gentle warming as needed to dissolve and then adding this blend to a separately prepared blend of the surfactants, homogenizing to a cream, and combining with a solution of water, organic nitrogen compound fixative, preservative, fragrance and other water soluble ingredients and then with the volatile liquid, and packaged in screw cap bottles.

The results show that the composition of the invention achieved the objective of imparting in a single application sufficient sunscreen to leave a person well protected even after a rinse test simulating real life conditions of bathing, showering, and rinsing.

EXAMPLE 14

A sunscreen containing body cleanser preparation that frothed upon placing upon the skin was formulated as shown below and tested by the method described above combining the measurement of static SPF and retention of SPF after the rinse test. All ingredients are shown in parts by weight.

| Ingredient | |
|---|---|
| Sunscreens: | |
| 2-ethylhexl p-methoxycinnamate | 5.63 |
| octyl salicylate | 3.75 |
| 2-hydroxy-4-methoxy-benzophenone | 4.5 |
| Anionic cleansing agent: | |
| Sodium Laureth sulfate | 3.85 |
| Sodium lauryl ether sulfate | 1.70 |
| Zwitterionic cleansing agent: Cocoylamidopropylbetaine | 3.33 |
| Volatile organic liquid: n-Pentane | 5.0 |
| Non-volatile organic liquid carrier: Petrolatum | 4.63 |
| Fixative: Polyquaternium 10 | 0.5 |
| Preservative: KATHON CG isothiazolidinone compound | 0.04 |
| Other ingredients: | |
| Cocoyldiethanolamide | 1.0 |
| Lauryl amine oxide | 0.75 |
| Fragrance | 1.0 |
| water | to 100 |
| pH | 6.5–7.5 |

The composition was prepared by first combining the sunscreens and petrolatum with gentle warming as needed to dissolve and then adding this blend to a separately prepared blend of the surfactants, homogenizing to a cream, and combining with a solution of water, organic nitrogen compound fixative, preservative, fragrance and other water soluble ingredients and then with the volatile liquid, and packaged in screw cap bottles.

The results show that the composition of the invention achieved the objective of imparting in a single application sufficient sunscreen to leave a person well protected even after a rinse test simulating real life conditions of bathing, showering, and rinsing.

EXAMPLE 15

A sunscreen containing body cleanser preparation that frothed upon placing upon the skin was formulated as shown above and tested by the method described below combining the measurement of static SPF and retention of SPF after the rinse test. All ingredients are shown in parts by weight.

| Ingredient | |
|---|---|
| Sunscreens: | |
| 2-ethylhexyl p-methoxycinnamate | 7.5 |
| 2-hydroxy-4-methoxy-benzophenone | 6.0 |
| Anionic cleansing agent: | |
| Sodium Laureth sulfate | 3.85 |
| Sodium lauryl ether sulfate | 1.05 |
| Zwitterionic cleansing agent: Cocoylamidopropylbetaine | 3.33 |
| Volatile organic liquid: n-Pentane | 5.0 |
| Non-volatile organic liquid carrier: Petrolatum | 5.0 |
| Fixative: Polyquaternium 10 | 0.5 |
| Preservative: KATHON CG isothiazolidinone compound | 0.04 |
| Other ingredients: | |
| Cocoyldiethanolamide | 3.33 |
| Lauryl amine oxide | 0.75 |
| Fragrance | 1.0 |
| water | to 100 |
| pH | 6.5–7.5 |
| Static SPF | 19.6 |
| SPF after rinse | 10.0 |

The composition was prepared by first combining the sunscreens and petrolatum with gentle warming as needed to dissolve and then adding this blend to a separately prepared blend of the surfactants, homogenizing to a cream, and combining with a solution of water, organic nitrogen compound fixative, preservative, fragrance and other water soluble ingredients and then with the volatile liquid, and packaged in screw cap bottles.

The results show that the composition of the invention achieved the objective of imparting in a single application sufficient sunscreen to leave a person well protected even after a rinse test simulating real life conditions of bathing, showering, and rinsing.

EXAMPLE 16

A sunscreen containing body cleanser preparation that frothed upon placing upon the skin was formulated as shown below and tested by the method described above combining the measurement of static SPF and retention of SPF after the rinse test. All ingredients are shown in parts by weight.

| Ingredient | |
|---|---|
| Sunscreens: | |
| 2-ethylhexyl p-methoxycinnamate | 5.63 |
| octyl salicylate | 3.75 |
| 2-hydroxy-4-methoxy-benzophenone | 4.5 |
| Anionic cleansing agent: | |
| Sodium Laureth sulfate | 3.85 |

-continued

| Ingredient | |
|---|---|
| Sodium lauryl ether sulfate | 1.05 |
| Zwitterionic cleansing agent: | 3.33 |
| Cocoylamidopropylbetaine | |
| Volatile organic | 5.0 |
| liquid: n-Pentane | |
| Non-volatile organic carrier: | 4.63 |
| 1-octadecene-maleic anhydride | |
| copolymer | |
| Fixative: | 0.5 |
| Polyquaternium 10 | |
| Preservative: | 0.04 |
| KATHON CG | |
| isothiazolidinone compound | |
| Other ingredients: | |
| Cocoyldiethanolamide | 3.33 |
| Lauryl amine oxide | 0.75 |
| Fragrance | 1.0 |
| water | to 100 |
| pH | 6.5–7.5 |

The composition was prepared by first combining the sunscreens and octadecene copolymer with gentle warming as needed to dissolve and then adding this blend to a separately prepared blend of the surfactants, homogenizing to a cream, and combining with a solution of water, organic nitrogen compound fixative, preservative, fragrance and other water soluble ingredients and then with the volatile liquid, and packaged in screw cap bottles.

The results show that the composition of the invention achieved the objective of imparting in a single application sufficient sunscreen to leave a person well protected even after a rinse test simulating real life conditions of bathing, showering, and rinsing.

EXAMPLE 17

A sunscreen containing body cleanser preparation that frothed upon placing upon the skin was formulated as shown below and tested by the method described above combining the measurement of static SPF and retention of SPF after the rinse test. All ingredients are shown in parts by weight.

| Ingredient | |
|---|---|
| Sunscreens: | |
| 2-ethylhexyl | 5.0 |
| p-methoxycinnamate | |
| octyl salicylate | 3.34 |
| 2-hydroxy-4-methoxy- | 4.0 |
| benzophenone | |
| Anionic cleansing agent: | |
| Sodium Laureth sulfate | 3.85 |
| Sodium lauryl ether sulfate | 1.05 |
| Zwitterionic cleansing agent: | 3.33 |
| Cocoylamidopropylbetaine | |
| Volatile organic | 5.0 |
| liquid: n-Pentane | |
| Non-volatile organic liquid | 6.16 |
| carrier: Petrolatum | |
| Fixative: | 0.5 |
| Polyquaternium 10 | |
| Preservative: | 0.04 |

-continued

| Ingredient | |
|---|---|
| KATHON CG | |
| isothiazolidinone compound | |
| Other ingredients: | |
| Cocoyldiethanolamide | 3.33 |
| Lauryl amine oxide | 0.75 |
| Fragrance | 1.0 |
| water | to 100 |
| pH | 6.5–7.5 |
| Static SPF | 22.0 |
| SPF after rinse | 10.0 |

The composition was prepared by first combining the sunscreens and petrolatum with gentle warming as needed to dissolve and then adding this blend to a separately prepared blend of the surfactants, homogenizing to a cream, and combining with a solution of water, organic nitrogen compound fixative, preservative, fragrance and other water soluble ingredients and then with the volatile liquid, and packaged in screw cap bottles.

The results show that the composition of the invention achieved the objective of imparting in a single application sufficient sunscreen to leave a person well protected even after a rinse test simulating real life conditions of bathing, showering, and rinsing.

EXAMPLES 18 AND 19, AND CONTROL B

Sunscreen containing body cleanser preparations according to the invention that frothed upon placing upon the skin, and a Control B composition lacking the non-volatile water immiscible carrier, were formulated as shown below and tested by the method described above combining the measurement of static SPF and retention of SPF after the rinse test. All ingredients are shown in parts by weight.

| Ingredient: | EX. 18 | EX. 19 | CONTROL B |
|---|---|---|---|
| Sunscreens: | | | |
| 2-ethylhexyl | 5.63 | 5.63 | 5.63 |
| p-methoxycinnamate | | | |
| octyl salicylate | 3.75 | 3.75 | 3.75 |
| 2-hydroxy-4-methoxy- | 4.5 | 4.5 | 4.5 |
| benzophenone | | | |
| Anionic cleansing agent: | | | |
| Sodium Laureth sulfate | 3.85 | 3.85 | 3.85 |
| Sodium lauryl ether sulfate | 1.05 | 1.05 | 1.05 |
| Zwitterionic cleansing agent: | 3.33 | 3.33 | 3.33 |
| Cocoylamidopropylbetaine | | | |
| Volatile organic liquid: | 5.0 | 5.0 | 5.0 |
| n-Pentane | | | |
| Non-volatile organic carrier: | 4.63 | NONE | NONE |
| Petrolatum | | | |
| 1-eicosene-vinylpyrrolidone | NONE | 4.63 | NONE |
| copolymer | | | |
| Fixative: | 0.5 | 0.5 | 0.5 |
| Polyquaternium 10 | | | |
| Preservative: | 0.04 | 0.04 | 0.04 |
| KATHON CG isothiazolidinone | | | |
| compound | | | |
| Other ingredients: | | | |
| Cocoyldiethanolamide | 3.33 | 3.33 | 3.33 |
| Lauryl amine oxide | 0.75 | 0.75 | 0.75 |
| Fragrance | 1.0 | 1.0 | 1.0 |

-continued

| Ingredient: | EX. 18 | EX. 19 | CONTROL B |
|---|---|---|---|
| water | to 100 | to 100 | to 100 |
| pH | 6.5–7.5 | 6.5–7.5 | 6.5–7.5 |

The composition was prepared by first combining the sunscreens and petrolatum or eicosene copolymer with gentle warming as needed to dissolve and then adding this blend to a separately prepared blend of the surfactants, homogenizing to a cream, and combining with a solution of water, organic nitrogen compound fixative, preservative, fragrance and other water soluble ingredients and then with the volatile liquid, and packaged in screw cap bottles.

The results show that the compositions of the invention achieved the objective of imparting in a single application sufficient sunscreen to leave a person well protected even after a rinse test simulating real life conditions of bathing, showering, and rinsing.

EXAMPLES 20–25

Sunscreen containing a basic body cleanser preparation according to the invention and additional compositions according the invention containing non-volatile water insoluble organic compound carriers were formulated as shown below and tested by the method described above combining the measurement of static SPF and retention of SPF after the rinse test. All ingredients are shown in parts by weight.

| Ingredient | EX. 20 | 21 | 22 | 23 | 24 | 25 |
|---|---|---|---|---|---|---|
| Sunscreens: | | | | | | |
| 2-ethylhexyl p-methoxy-cinnamate | 7.5 | 7.5 | 7.5 | 7.5 | 7.5 | 7.5 |
| octyl salicylate | 5.0 | NONE | 5.0 | 5.0 | 5.0 | 5.0 |
| 2-hydroxy-4-methoxy-benzophenone | 6.0 | 6.0 | 6.0 | 5.0 | 6.0 | 6.0 |
| Anionic cleansing agent: | | | | | | |
| Sodium Laureth sulfate | 3.85 | 3.85 | 3.85 | 3.85 | 3.85 | 3.85 |
| Sodium lauryl ether sulfate | 1.05 | 1.05 | 1.05 | 1.05 | 1.05 | 1.05 |
| Zwitterionic cleansing agent: Cocoylamidopropylbetaine | 3.33 | 3.33 | 3.33 | 3.33 | 3.33 | 3.33 |
| Non-volatile carrier: | NONE | 5.0 | 5.0 | NONE | NONE | NONE |
| Petrolatum | | | | | | |
| C12–C15 Alkylbenzoate | NONE | NONE | NONE | 5.0 | NONE | NONE |
| GE SF1528 Cyclomethicone Dimethicone Copolyol | NONE | NONE | NONE | NONE | 6.0 | 12.0 |
| Fixative: Polyquaternium 10 | 0.5 | 0.5 | 0.5 | 0.5 | 0.5 | 0.5 |
| Preservative: | 0.04 | 0.04 | 0.04 | 0.04 | 0.04 | 0.04 |

-continued

| Ingredient | EX. 20 | 21 | 22 | 23 | 24 | 25 |
|---|---|---|---|---|---|---|
| KATHON CG isothiazolidinone compound Other ingredients: | | | | | | |
| Cocoyldiethanolamide | 3.33 | 3.33 | 3.33 | 3.33 | 3.33 | 3.33 |
| Lauryl amine oxide | 0.75 | 0.75 | 0.75 | 0.75 | 0.75 | 0.75 |
| water | to 100 | to 100 | to 100 | to 100 | to 100 | to 100 |
| pH | 6.7 | 6.7 | 6.7 | 6.7 | 6.7 | 6.7 |

The composition was prepared by first combining the sunscreens and carrier liquid when present with gentle warming as needed to dissolve and then adding this blend to a separately prepared blend of the surfactants, homogenizing to a cream, and combining with a solution of water, organic nitrogen compound fixative, preservative, and other water soluble ingredients, and packaged in screw cap bottles.

The following results were obtained:

| | | | | | | |
|---|---|---|---|---|---|---|
| Static SPF | 23.0 | 22.3 | 24.5 | 25.7 | 24.5 | 24.5 |
| SPF after rinse | 9.4 | 11.7 | 9.0 | 10.5 | 6.4 | 6.4 |

The results show that the compositions of the invention achieved the objective of imparting in a single application sufficient sunscreen to leave a person well protected even after a rinse test simulating real life conditions of bathing, showering, and rinsing.

EXAMPLES 26–28

Sunscreen containing body cleanser preparations according to the invention containing petrolatum as non-volatile carrier, were formulated as shown below and tested by the method described above combining the measurement of static SPF and retention of SPF after the rinse test. All ingredients are shown in parts by weight.

| Ingredient | EX. 26 | EX. 27 | EX. 28 |
|---|---|---|---|
| Sunscreens: | | | |
| 2-ethylhexyl p-methoxycinnamate | 7.5 | 7.5 | 7.5 |
| octyl salicylate | 5.0 | 5.0 | 5.0 |
| 2-hydroxy-4-methoxy-benzophenone | 6.0 | 6.0 | 6.0 |
| Octocrylene | NONE | 5.0 | 7.0 |
| Anionic cleansing agent: | | | |
| Sodium Laureth sulfate | 3.3 | 3.3 | 3.0 |
| Sodium lauryl ether sulfate | 1.05 | 1.05 | 1.05 |
| Zwitterionic cleansing agent: Cocoylamidopropylbetaine | 2.85 | 2.85 | 2.6 |
| Non-volatile organic carrier: Petrolatum | 10.0 | 5.0 | 5.0 |
| Fixative: Polyquaternium 10 | 0.5 | 0.5 | 0.5 |
| Preservative: KATHON CG isothiazolidinone compound | 0.04 | 0.04 | 0.04 |

-continued

| Ingredient | EX. 26 | EX. 27 | EX. 28 |
|---|---|---|---|
| Other ingredients: | | | |
| Cocoyldiethanolamide | 4.0 | 4.0 | 3.8 |
| Lauryl amine oxide | 0.75 | 0.75 | 0.75 |
| water | to 100 | to 100 | to 100 |
| pH | 6.5–7.5 | 6.5–7.5 | 6.5–7.5 |

The composition was prepared by first combining the sunscreens and petrolatum with gentle warning as needed to dissolve and then adding this blend to a separately prepared blend of the surfactants, homogenizing to a cream, and combining with a solution of water, organic nitrogen compound fixative, preservative, and other water soluble ingredients, and packaged in screw cap bottles.

The following results were obtained:

| Static SPF | 22.5 | 20.3 | 22.5 |
|---|---|---|---|
| SPF after rinse | 8.3 | 9.4 | 10.3 |

The results show that the compositions of the invention achieved the objective of imparting in a single application sufficient sunscreen to leave a person well protected even after a rinse test simulating real life conditions of bathing, showering, and rinsing.

EXAMPLES 29–32

Sunscreen containing body cleanser preparations according to the invention including a commercial silicone-treated zinc oxide in the combined sunscreen agents were formulated as shown below and tested by the method described above combining the measurement of static SPF and retention of SPF after the rinse test. All ingredients are shown in parts by weight.

| Ingredient: | EX. 29 | EX. 30 | EX. 31 | EX. 32 |
|---|---|---|---|---|
| Sunscreens: | | | | |
| 2-ethylhexyl p-methoxycinnamate | 7.5 | 7.5 | 7.5 | 7.5 |
| octyl salicylate | 5.0 | 5.0 | 5.0 | 5.0 |
| 2-hydroxy-4-methoxy-benzophenone | NONE | 6.0 | 5.0 | 6.0 |
| Octocrylene | NONE | 5.0 | 7.0 | NONE |
| Zinc oxide | 5.0 | 5.0 | 5.0 | 5.0 |
| Anionic cleansing agent: | | | | |
| Sodium Laureth sulfate | 3.75 | 3.5 | 3.5 | 3.85 |
| Sodium lauryl ether sulfate | 1.05 | 1.05 | 1.05 | 1.05 |
| Zwitterionic cleansing agent: Cocoylamidopropylbetaine | 3.25 | 3.0 | 3.0 | 3.33 |
| Fixative: Polyquaternium 10 | 0.5 | 0.5 | 0.5 | 0.5 |
| Preservative: KATHON CG isothiazolidinone compound | 0.04 | 0.04 | 0.04 | 0.04 |
| Other ingredients: | | | | |
| Cocoyldiethanolamide | 4.3 | 4.1 | 4.1 | 4.33 |
| Lauryl amine oxide | 0.75 | 0.75 | 0.75 | 0.75 |
| water | to 100 | to 100 | to 100 | to 100 |
| pH | 6.5–7.5 | 6.5–7.5 | 6.5–7.5 | 6.5–7.5 |

The composition was prepared by first combining the sunscreens with gentle warming and then adding this blend to a separately prepared blend of the surfactants, homogenizing to a cream, and combining with a solution of water, organic nitrogen compound fixative, preservative, and other water soluble ingredients, and packaged in screw cap bottles.

The following results were obtained:

| Static SPF | 24.5 | 30.6 | 30.6 | 28.7 |
|---|---|---|---|---|
| SPF after rinse | 8.2 | 9.0 | 10.0 | 13.3 |

The results show that the composition of the invention achieved the objective of imparting in a single application sufficient sunscreen to leave a person well protected even after a rinse test simulating real life conditions of bathing, showering, and rinsing.

EXAMPLES 33–35

Sunscreen containing body cleanser preparations according to the invention containing a commercial grade of silicone-treated zinc oxide among the sunscreen agents and a non-volatile compound carrier were formulated as shown below and tested by the method described above combining the measurement of static SPF and retention of SPF after the rinse test. All ingredients are shown in parts by weight.

| Ingredient: | EX. 33 | EX. 34 | EX. 35 |
|---|---|---|---|
| Sunscreens: | | | |
| 2-ethylhexyl p-methoxycinnamate | 7.5 | 7.5 | 7.5 |
| octyl salicylate | 5.0 | 5.0 | 5.0 |
| 2-hydroxy-4-methoxy-benzophenone | 5.0 | 5.0 | 6.0 |
| zinc oxide | 5.0 | 5.0 | 5.0 |
| Anionic cleansing agent: | | | |
| Sodium Laureth sulfate | 3.5 | 3.5 | 3.5 |
| Sodium lauryl ether sulfate | 1.05 | 1.05 | 1.05 |
| Zwitterionic cleansing agent: Cocoylamidopropylbetaine | 3.0 | 3.0 | 3.0 |
| Non-volatile organic carrier | | | |
| Petrolatum | 5.0 | 5.0 | NONE |
| C12–C15 Alkyl benzoate | NONE | 5.0 | 5.0 |
| Fixative: Polyquaternium 10 | 0.5 | 0.5 | 0.5 |
| Preservative: KATHON CG isothiazolidinone compound | 0.04 | 0.04 | 0.04 |
| Other ingredients: | | | |
| Cocoyldiethanolamide | 4.1 | 4.1 | 4.1 |
| Lauryl amine oxide | 0.75 | 0.75 | 0.75 |
| water | to 100 | to 100 | to 100 |
| pH | 6.5–7.5 | 6.5–7.5 | 6.5–7.5 |

The composition was prepared by first combining the sunscreens and petrolatum oralkyl benzoate with gentle warming as needed to dissolve and then adding this blend to a separately prepared blend of the surfactants, homogenizing to a cream, and combining with a solution of water, organic nitrogen compound fixative, preservative, and other water soluble ingredients, and packaged in screw cap bottles.

The following results were obtained:

| Static SPF | 27.5 | 25.7 | 25.7 |
|---|---|---|---|
| SPF after rinse | 11.8 | 11.9 | 13.2 |

The results show that the composition of the invention achieved the objective of imparting in a single application sufficient sunscreen to leave a person well protected even after a rinse test simulating real life conditions of bathing, showering, and rinsing.

We claim:

1. A body cleansing composition providing upon a single application to a person in need of protection against sunburn protection measured by Sun Protection Factor (SPF) of at least 15 as applied and SPF of at least at least 4 after rinsing, consisting essentially of water, the amount of water being in the range from 30 to 90 parts by weight; at least one first sunscreen compound which is a paramethoxycinnamate ester, and at least one second sunscreen compound able to absorb at least 50% of incident radiation at wave lengths from 290 to 320 nanometers and selected from the group consisting of a 2-hydroxy-4-alkoxybenzophenone, a salicylic acid ester, octocrylene, zinc oxide and mixtures thereof, in which the combined amounts of first sunscreen compound and second sunscreen compound are in the range from 3 to 40 parts by weight; a combination of at least two surface active agents including a first anionic agent which is an alkyl sulfate salt or an alkoxylated alkyl sulfate salt, and a second agent which is nonionic, anionic or zwitterionic, provided that when said second agent is anionic it is not identical with said first anionic agent, the amount of first anionic agent being in the range from 3 to 15 parts by weight and the amount of second surface active agent being in the range from 1 to 10 parts by weight; at least one hydroxyethylated organic nitrogen compound fixative to enhance retention of SPF on the user's skin selected from the group consisting of N-(2-hydroxyethyl)lactamide and a polymeric quaternary ammonium salt having a plurality of quaternary ammonium groups and at least one 2-hydroxyethyl group, the amount of N-(2-hydroxyethyl)lactamide being in the range from 0 to 12 parts by weight and the amount of polymeric 2-hydroxyethyl quaternary ammonium salt being in the range from 0 to 1 part by weight, provided that said amounts are not simultaneously 0; and at least one additive selected from the group consisting of non-aggressive volatile organic liquids boiling within the range of 15 to 60° C., water-immiscible non-volatile organic carriers, and preservatives able to retard microbial spoilage, the amount of non-aggressive volatile organic liquid being in the range from 0 to 12 parts by weight, the amount of water-immiscible non-volatile organic liquid being in the range from 0 to 25 parts by weight, and the amount of preservative being in the range from 0 to 2 parts by weight, provided that the amounts of each such additive are not simultaneously 0; whereby protection against sunburn is imparted to a person in need thereof in a single application of said composition.

2. A composition according to claim 1 in which the first sunscreen compound is selected from the group consisting of 2-ethylhexyl p-methoxycinnamate, 2-ethoxyethyl p-methoxycinnamate, diethanolamine p-methoxycinnamate, n-octyl p-methoxycinnamate and mixtures thereof.

3. A composition according to claim 1 in which the second sunscreen compound includes zinc oxide with particle size in the range from 2 to 50 microns.

4. A composition according to claim 1 in which the first surface active agent is selected from the group consisting of ammonium lauryl sulfate, sodium laureth sulfate, sodium lauryl ether sulfate and mixtures thereof.

5. A composition according to claim 1 in which the zwitterionic agent is selected from the group consisting of fatty acylamidopropylhydroxysultaine, fatty acylamidopropylbetaine and mixtures thereof in which the fatty acyl group contains from 8 to 18 carbon atoms.

6. A composition according to claim 5 in which the zwitterionic agent is cocoylamidopropylbetaine.

7. A composition according to claim 1 in which the fixative organic nitrogen compound is N-(2-hydroxyethyl) lactamide.

8. A composition according to claim 1 in which the fixative organic nitrogen compound is selected from the group consisting of Polyquaternium 1, Polyquaternium 4, Polyquaternium 10, and Polyquaternium 24.

9. A composition according to claim 8 in which the fixative organic nitrogen compound is Polyquaternium 10.

10. A composition according to claim 1 in which the additive is at least one preservative selected from the group consisting of butyl paraben, methyl paraben, propyl paraben, imidazolidinylurea, dimethyloldimethylhydantoin, an isothiazolidone compound and mixtures thereof.

11. A composition according to claim 1 frothing after being placed on the skin of a person in which a non-aggressive volatile organic compound additive is an aliphatic or cycloaliphatic hydrocarbon.

12. A composition according to claim 11 in which the hydrocarbon is pentane.

13. A composition according to claim 1 whereby protection measured by SPF after rinsing of at least 5 is imparted by a single application thereof.

14. A composition according to claim 1 frothing after being placed on the skin of a person in which a non-aggressive volatile organic compound additive is a polyhalogenated organic compound in which at least one halogen is fluorine.

15. A composition according to claim 1 in which a water-immiscible non-volatile organic carrier additive is selected from the group consisting of high molecular weight hydrocarbons with at least 30 carbon atoms, esters having from 16 to 60 carbon atoms, silicone oils, and modified silicones.

16. A composition according to claim 15 in which the water-immiscible organic carrier additive is petrolatum.

17. A composition according to claim 15 in which the water-immiscible organic carrier additive is C12–C15 alkyl benzoate.

18. The method of imparting to a person in need thereof protection against sunburn measured by Sun Protection Factor of at least 15 as applied and at least 4 after rinsing, comprising applying once to the body of said person a body cleansing composition according to claim 1, allowing said composition to remain on said person for a dwell period, and rinsing the person's body, thereby imparting protection against sunburn.

19. The method according to claim 18 in which the quantity of composition applied is in the range from 5 to 100 grams.

20. The method according to claim 18 in which the dwell period is in the range from 15 seconds to 5 minutes.

21. The method according to claim 18 in which the composition includes a fixative selected from the group consisting of Polyquaternium 1, Polyquaternium 4, Polyquaternium 10, and Polyquaternium 24.

22. The method according to claim 18 in which the composition includes a non-aggressive volatile organic liquid boiling in the range from 15 to 60øC.

23. The method according to claim 18 in which the composition includes a water insoluble non-volatile organic compound carrier.

24. A composition according to claim 1 including 4 to 8 parts by weight of 2-ethylhexyl p-methoxycinnamate, 0 to 6 parts by weight of octyl salicylate, 3 to 8 parts by weight of 2-hydroxy-4-methoxybenzophenone, 6 to 9 parts by weight of ammonium lauryl sulfate, 1 to 2 parts of sodium cocoyl isethionate, 2 to 5 parts by weight of cocoylamidopropylhydroxysultaine, 0.3 to 0.6 parts by weight of Polyquaternium 10, and 0.02 to 1 part by weight of preservative.

25. A composition according to claim 1 including 4 to 8 parts by weight of 2-ethylhexyl p-methoxycinnamate, 3 to 8 parts by weight of octyl salicylate, 0 to 6 parts by weight of 2-hydroxy-4-methoxybenzophenone, 3 to 6 parts by weight of sodium laureth sulfate, 2 to 5 parts by weight of cocoylamidopropylbetaine, 0.3 to 0.6 parts by weight of Polyquaternium 10, and 0.02 to 0.1 part of preservative.

26. A composition according to claim 1 including 4 to 8 parts by weight of 2-ethylhexyl p-methoxycinnamate, 0 to 6 parts by weight of octyl salicylate, 3 to 8 parts by weight of 2-hydroxy-4-methoxybenzophenone, 3 to 6 parts by weight of sodium laureth sulfate, 2 to 5 parts by weight of cocoylamidopropylbetaine, 0.3 to 0.6 parts by weight of Polyquaternium 10, 3 to 10 parts by weight of pentane, 3 to 10 parts by weight of petrolatum, and 0.02 to 1 part by weight of preservative.

27. A composition according to claim 1 including 4 to 8 parts by weight of 2-ethylhexyl p-methoxycinnamate, 0 to 6 parts by weight of octyl salicylate, 3 to 8 parts by weight of 2-hydroxy-4-methoxybenzophenone, 3 to 6 parts by weight of sodium laureth sulfate, 2 to 5 parts by weight of cocoylamidopropylbetaine, 0.3 to 0.6 parts by weight of Polyquaternium 10, 5 to 10 parts of petrolatum, and 0.02 to 0.1 part of preservative.

28. The method according to claim 21 in which the composition includes 4 to 8 parts by weight of 2-ethylhexyl p-methoxycinnamate, 0 to 6 parts by weight of octyl salicylate, 3 to 8 parts by weight of 2-hydroxy-4-methoxybenzophenone, 3 to 6 parts by weight of sodium laureth sulfate, 2 to 5 parts by weight of cocoylamidopropylbetaine, 0.3 to 0.6 parts by weight of Polyquaternium 10, and 0.02 to 1 part by weight of preservative.

29. The method according to claim 21 in which the composition includes 4 to 8 parts by weight of 2-ethylhexyl p-methoxycinnamate, 0 to 6 parts by weight of octyl salicylate, 3 to 8 parts by weight of 2-hydroxy-4-methoxybenzophenone, 3 to 6 parts by weight of sodium laureth sulfate, 2 to 5 parts by weight of cocoylamidopropylbetaine, 0.3 to 0.6 parts by weight of Polyquaternium 10, 3 to 10 parts by weight of pentane, 3 to 10 parts by weight of petrolatum, and 0.02 to 1 part by weight of preservative.

30. The method according to claim 21 in which the composition includes 4 to 8 parts by weight of 2-ethylhexyl p-methoxycinnamate, 3 to 8 parts by weight of octyl salicylate, 0 to 6 parts by weight of 2-hydroxy-4-methoxybenzophenone, 3 to 6 parts by weight of sodium laureth sulfate, 2 to 5 parts by weight of cocoylamidopropylbetaine, 0.3 to 0.6 parts by weight of Polyquaternium 10, 3 to 10 parts by weight of petrolatum, and 0.02 to 1 part by weight of preservative.

* * * * *